US00PP09811P

United States Patent [19]

VandenBerg

[11] Patent Number: Plant 9,811

[45] Date of Patent: Feb. 25, 1997

[54] CHRYSANTHEMUM PLANT NAMED 'BRISA'

[75] Inventor: Cornelis P. VandenBerg, Salinas, Calif.

[73] Assignee: Yoder Brothers, Inc., Barberton, Ohio

[21] Appl. No.: 615,799

[22] Filed: Mar. 14, 1996

[51] Int. Cl.[6] ..... A01H 5/00

[52] U.S. Cl. ..... Plt./77

[58] Field of Search ..... Plt./77

[56] References Cited

U.S. PATENT DOCUMENTS

P.P. 7,518 5/1991 VandenBerg ..... Plt./77

*Primary Examiner*—Howard J. Locker
*Attorney, Agent, or Firm*—Foley & Lardner

[57] ABSTRACT

A Chrysanthemum plant named Brisa particularly characterized by its small pompon capitulum form; formal decorative capitulum type; white ray floret color; diameter across face of capitulum of 32 to 38 mm when fully opened; flowering response in Salinas under normal temperatures is 52 to 56 days after start of short days; flowering response in Bogota, Colombia is 68 to 69 days after start of short days; plant height is 81 to 86 cm when grown in Salinas with 18 long days prior to start of short days; height is 99 to 122 cm when grown in Bogota, Colombia with 21 to 22 long days prior to start of short days; peduncle length of the first and the fourth laterals at flowering after removing the apical bud is 5 to 8 cm and 8 cm when gronw in Salinas; peduncle length when grown in Bogota, Colombia is 10 to 20 cm and 15 to 23 cm, respectively; production of 16 to 18 laterals, each producing one terminal flower when grown in Salinas; production is 10 to 13 laterals when grown in Bogota, Colombia; and uniform flowering in year round flowerings.

1 Drawing Sheet

The present invention comprises a new and distinct cultivar of Chrysanthemum, botanically known as *Dendranthema grandiflora,* and referred to by the cultivar name Brisa.

Brisa, identified as 2813 (92-D86001), was originated from a cross made by Cornelis P. VandenBerg in a controlled breeding program in Salinas, Calif., in June of 1992.

The male parent of Brisa was an the cultivar identified as Nimba, disclosed in U.S. Plant Pat. No. 6,947, and described as a cut spray mum with a small pompon capitulum form, a formal decorative capitulum type and a white ray floret color.

The female parent of Brisa was an unnamed seedling, identified as 1571 (89-918001) and described as a cut spray mum with a small pompon capitulum form, a formal decorative capitulum type with many disc florets, and a white ray floret color.

Brisa was discovered and selected as one flowering plant within the progeny of the stated cross by Cornelis P. VandenBerg in April of 1993, in a controlled environment in Salinas, Calif.

The first act of asexual reproduction of Brisa was accomplished when vegetative cuttings were taken from the initial selection in June of 1993 in a controlled environment in Salinas, Calif., by technicians working under supervision of Cornelis P. VandenBerg.

Horticultural examination of controlled flowerings of successive plantings has shown that the unique combination of characteristics as herein disclosed for Brisa are firmly fixed and are retained through successive generations of asexual reproduction. Brisa has not been observed under all possible environmental conditions. The phenotype may vary significantly with variations in environment such as temperature, light intensity and daylength, without, however, any variance in genotype.

The following observations measurements and comparisons describe plants grown in Salinas, Calif., and near Bogota, Colombia, South America under greenhouse conditions which approximate those generally used in commerical greenhouse practice.

The following traits have been repeatedly observed and are determined to be basic characteristics of Brisa, which, in combination, distinguish this Chrysanthemum as a new and distinct cultivar:

1. Small pompon capitulum form.
2. Formal decorative capitulum type.
3. White ray floret color.
4. Diameter across face of capitulum of 32 to 38 mm when fully opened.
5. Flowering response in Salinas under normal temperatures is 52 to 56 days after start of short days. Flowering response in Bogota, Colombia is 68 to 69 days after start of short days.
6. Plant height is 81 to 86 cm when grown in Salinas with 18 long days prior to start of short days; height is 99 to 122 cm when grown in Bogota, Colombia with 21 to 22 long days prior to start of short days.
7. Peduncle length of the first and the fourth laterals at flowering after removing the apical bud is 5 to 8 cm and 8 cm when grown in Salinas; peduncle length when grown in Bogota, Colombia is 10 to 20 cm and 15 to 23 cm, respectively.
8. Production of 16 to 18 laterals, each producing one terminal flower when grown in Salinas. Production is 10 to 13 laterals when grown in Bogota, Colombia.
9. Uniform flowering in year round flowerings.

The accompanying photographic drawing is a side view of a cut spray mum of Brisa, showing typical inflorescence and leaf characteristics of Brisa, with the colors being as nearly true as possible with illustrations of this type.

Of the commercial cultivars known to the inventor, the most similar in comparison to Brisa is the female parent Nimba. Reference is made to attached Chart A, which compares certain characteristics of Brisa with the same characteristics of Nimba. Nimba does not flower under the environmental conditions of Bogota, and comparisons are made only of plants grown in Salinas, Calif. Similar traits are ray floret color, and capitulum form and type. The flowering response to short days of Brisa and Nimba is comparable. When compared with Nimba, Brisa has a smaller diameter of capitulum, a shorter plant height, and shorter peduncles than Nimba. In addition, Nimba often shows disc florets in the center of the flower, while Brisa does not show any disc florets.

In the following description color references are made to The Royal Horticultural Society Colour Chart. The color values were determined on plant material grown as a single stem spray cut mum in Salinas, Calif. on May 24, 1995.

Classification:

*Botanical.*—Dendranthema grandiflora cv Brisa.

*Commercial.*—Small pompon formal decorative spray cut mum.

INFLORESCENCE

A. Capitulum:

*Form.*—Small pompon.

*Type.*—Formal decorative.

*Diameter across face.*—32 to 38 mm when fully opened.

B. Corolla of ray florets:

*Color (general) tonality from a distance of three meters).*—White.

*Color (upper surface).*—155D.

*Color (under surface).*—155D.

*Shape.*—Cross-section concave, longitudinal section straight.

C. Corolla of disc florets:

*Color (mature).*—No disc florets present.

*Color (immature).*—No disc florets present.

D. Reproductive Organs:

*Androecium.*—No disc florets present.

*Gynoecium.*—Present on ray florets.

PLANT

A. General appearance:

*Height.*—81 to 86 cm when grown in Salinas with 18 long days prior to start of short days; height is 99 to 122 cm when grown in Bogota, Colombia with 21 to 22 long days prior to start of short days.

B. Foliage:

*Color (upper surface).*—147A.

*Color (under surface).*—147B.

*Shape.*—Lobed and serrated.

CHART A

COMPARISON OF BRISA AND NIMBA

| CHARACTERISTIC | BRISA | NIMBA |
|---|---|---|
| Ray floret color | White | White |
| Capitulum form and type | Small pompon Formal decorative | Small pompon Formal decorative |
| Diameter across face of capitulum | 32 to 38 mm | 38 to 45 mm |
| Flowering response | 52 to 56 days | 50 to 56 days |
| Plant height with 18 long days | 81 to 86 cm | 89 to 104 cm |
| Penduncle length | | |
| 1st lateral | 5 to 8 cm | 8 to 10 cm |
| 4th lateral | 8 cm | 10 to 13 cm |

COMPARISONS MADE OF PLANTS GROWN AS SINGLE STEM SPRAY CUT MUMS IN SALINAS, CALIFORNIA

What is claimed:

1. A new and distinct Chrysanthemum plant named Brisa, as described and illustrated.

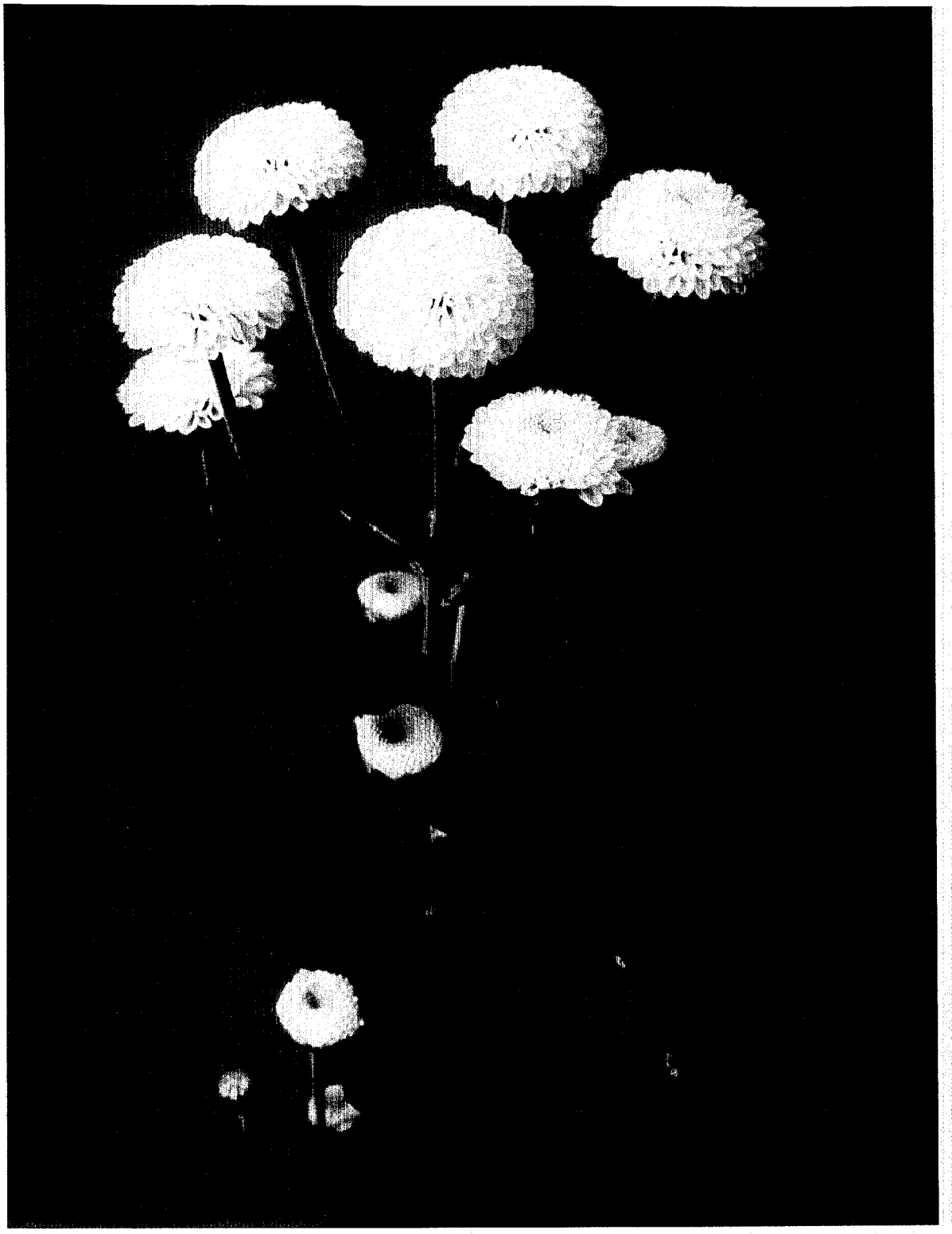

* * * * *